(12) United States Patent
Niemiec et al.

(10) Patent No.: US 7,035,168 B2
(45) Date of Patent: Apr. 25, 2006

(54) POWER CONTROL FOR INSTRUMENTED MEDICATION PACKAGE

(75) Inventors: Mark A. Niemiec, Ponte Vedra, FL (US); Louis M. Heidelberger, Villanova, PA (US)

(73) Assignee: DDMS Holdings, L.L.C., Ponte Vedra, FL (US)

( * ) Notice: Subject to any disclaimer, the term of this patent is extended or adjusted under 35 U.S.C. 154(b) by 499 days.

(21) Appl. No.: 10/234,021

(22) Filed: Sep. 3, 2002

(65) Prior Publication Data

US 2003/0111477 A1    Jun. 19, 2003

Related U.S. Application Data

(63) Continuation-in-part of application No. 09/901,475, filed on Jul. 9, 2001, now Pat. No. 6,574,166, which is a continuation-in-part of application No. 09/611,582, filed on Jul. 7, 2000, now Pat. No. 6,411,567.

(51) Int. Cl.
*G04B 47/00* (2006.01)
*B65D 83/04* (2006.01)

(52) U.S. Cl. ........................ 368/10; 206/528; 206/531; 221/2

(58) Field of Classification Search ................. 368/10; 206/531–534; 221/2, 3, 15
See application file for complete search history.

(56) References Cited

U.S. PATENT DOCUMENTS

| | | | | |
|---|---|---|---|---|
| 4,258,354 A | * | 3/1981 | Carmon et al. | 340/309.4 |
| 4,526,474 A | * | 7/1985 | Simon | 368/10 |
| 4,617,557 A | * | 10/1986 | Gordon | 340/309.7 |
| 4,971,221 A | * | 11/1990 | Urquhart et al. | 221/2 |
| 5,313,439 A | * | 5/1994 | Albeck | 368/10 |
| 5,751,661 A | * | 5/1998 | Walters | 368/10 |
| 6,633,796 B1 | * | 10/2003 | Pool et al. | 700/231 |

* cited by examiner

*Primary Examiner*—Vit W. Miska
(74) *Attorney, Agent, or Firm*—Reed Smith LLP

(57) ABSTRACT

The present invention is method for switching a power supply associated with an instrumented medication package, such that energy contained in the power supply can be preserved until the instrumented medication package is dispensed to a patient. The switch may be formed by providing an exposed discontinuity on a trace forming a conductive path between the power supply and circuitry associated with the instrumented medication package. Bridging the discontinuity, such as by placing a conductive element across the discontinuity, allows the power supply to be conductively connected to the circuitry, such that the circuitry can perform its desired function.

9 Claims, 6 Drawing Sheets

POWER CONTROL FOR INSTRUMENTED MEDICATION PACKAGE

The present patent application is a continuation in part of U.S. patent application Ser. No. 09/901,475, filed Jul. 9, 2001, now U.S. Pat. No. 6,574,166 which is a continuation in part of U.S. patent application Ser. No. 09/611,582, filed Jul. 7, 2000, now registered as U.S. Pat. No. 6,411,567.

FIELD OF THE INVENTION

The present invention pertains to the control of power within an instrumented medication package, and more particularly to the creation of an inexpensive means for allowing a power supply circuit to be completed when an instrumented medication package is dispensed.

BACKGROUND OF THE INVENTION

Medication packages which utilize electronic circuitry to provide functionality in association with the medication package are being developed as a means to improve the effectiveness of the medicine contained within the packaging, as well as to assist in the prevention of ill effects associated with the improper usage of the medication. The electronic circuits integrated with the medication packaging may utilize a power supply to provide electrical potential to allow the circuits to function. Present power supplies are limited, however, in that power supplies provided by the manufacturer of a medication package may be required to sit on a shelf for a protracted period of time before the medication package is dispensed to a patient. If the circuitry is active while the package sits on a shelf, the power supply may be exhausted before the package is ever dispensed to a patient. Accordingly, one prior art reference has described providing a charger at a pharmacy to allow the power supply to be recharged immediately before the package is dispensed. Although this may ensure that the power supply on the medication package is charged, this method also requires pharmacists to begin charging a medication several hours before the package is dispensed, thus limiting the ability to dispense medication on a walk in basis. A patient would be prevented from walking into the pharmacy, prescription in hand, and walking out a short period later with medication in an instrumented medication package. Alternately, the provision of a removable power supply or supplies, limits the efficiency with which the instrumented medication packaging can be produced, as well as increases the cost of the packaging.

SUMMARY OF THE INVENTION

The present invention is an instrumented medication package having a switched power supply for circuitry associated with the instrumented medication package, such that energy contained in the power supply can be preserved until the instrumented medication package is dispensed to a patient. The switch may be formed by providing an exposed discontinuity on a trace forming a conductive path between the power supply and circuitry associated with the instrumented medication package. Bridging the discontinuity, such as by placing a conductive element across the discontinuity, allows the power supply to be conductively connected to the circuitry, such that the circuitry can perform its desired function.

The present invention may be embodied in an instrumented medication package having a power supply, circuitry for monitoring at least one condition associated with the instrumented medication package, and a connective path between said power supply and said circuitry, where a switch is provided to interrupt the connective path between the power supply and the instrumented medication package circuitry.

The present invention may also be embodied in an instrumented medication package, where the connective path includes an exposed discontinuity, such that a bridging element may be placed across the discontinuity to complete the circuit between the power supply and the instrumented medication package circuitry. The bridging element may be a switch label having a conductive side, such that placing the conductive layer across the discontinuity will complete the circuit. Additionally, the reverse side of the switch label may be an insulative material, such that the switch label may be placed across the discontinuity with the insulative material covering the discontinuity, such that an electrical path is not completed, but the discontinuity is protected.

DETAILED DESCRIPTION OF THE INVENTION

For the purposes of the present description, the present invention is described in association with an instrumented medication package as described in Applicant's U.S. patent application Ser. No. 09/611,582, now U.S. Pat. No. 6,411,567 and Applicant's U.S. patent application Ser. No. 09/901,475. These references are herein incorporated in their entireties by reference thereto. The specific embodiments of the instrumented medication package as described in Applicant's previous patent applications are not intended to limit the scope of the presently claimed invention.

Figure 1:
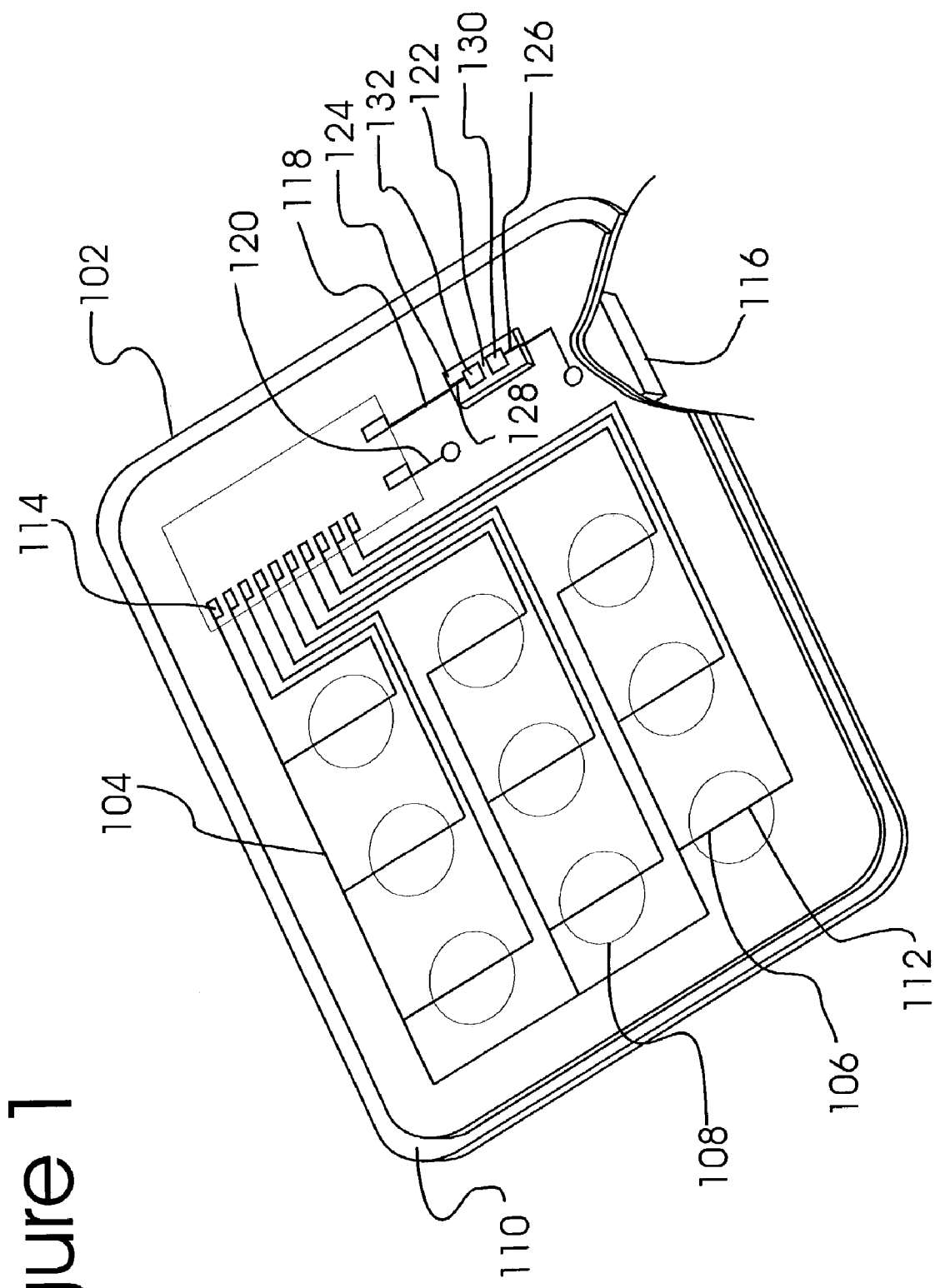
FIG. 1 illustrates a notional printed circuit scheme for an instrumented medication package.

In FIG. 1, wherein like numbers represent like elements, there is shown an instrumented medication package 102 utilizing printed circuitry 104 to locate severable conductors 106 over the openings 108 of a plurality of medication containment cells (not visible in view shown). As previously disclosed, a barrier layer 110 may be located over a blister package having a plurality of containment cells. The barrier layer 110 may form a closure over the containment cells, protecting medication contained in the cells from environmental effects.

Severable conductors 106 may be formed by printing conductive traces 112 over the containment cells, such that an individual accessing medication contained in the cells severs the conductive traces 112, causing a discontinuity in the conductive traces 112. The conductive traces 112 may be printed to allow contact pads 114 to be formed, allowing monitoring and communications circuitry formed in a separate chip (not shown) to be located over the pads 114, allowing the presence of a severed severable conductor to be communicated to the chip.

As shown in Applicant's U.S. patent application Ser. No. 09/901,475, a power supply 116 for providing energy circuitry 104 on the instrumented medication package 102 may be provided on the side of the instrumented medication package 107 from which containment cells extend, such that the use of surface area on the instrumented medication package may be maximized. Conductive leads 118, 120 extending from the power supply 116 may extend through the instrumented medication package, allowing the power supply package 116 to provide energy to a chip on the opposite side of the instrumented medication package.

A first power supply trace 118 used for conducting electrical energy from the power supply 116 to circuitry may be provided with a discontinuity 122, while a second power trace 120 may be complete between the power supply 116 and the instrumented medication package circuitry 104. The presence of the discontinuity 122 prevents the electrical energy of the power source 116 from being conducted to the circuitry 104. The discontinuity 122 may be printed over a second block of insulative material 124 to space the discontinuity away from the barrier layer 110. The discontinuity 122 may be formed by skipping printing for a portion of the path the first power supply trace would otherwise take. The ends 126, 128 of the skipped portion may be provided with oversize pads 130, 132 to provide improved contact with a conductive element, should it be desired to energize the circuitry 104 of the instrumented medication package 102 by connecting the power supply 116 to the circuitry 104.

Figure 2:
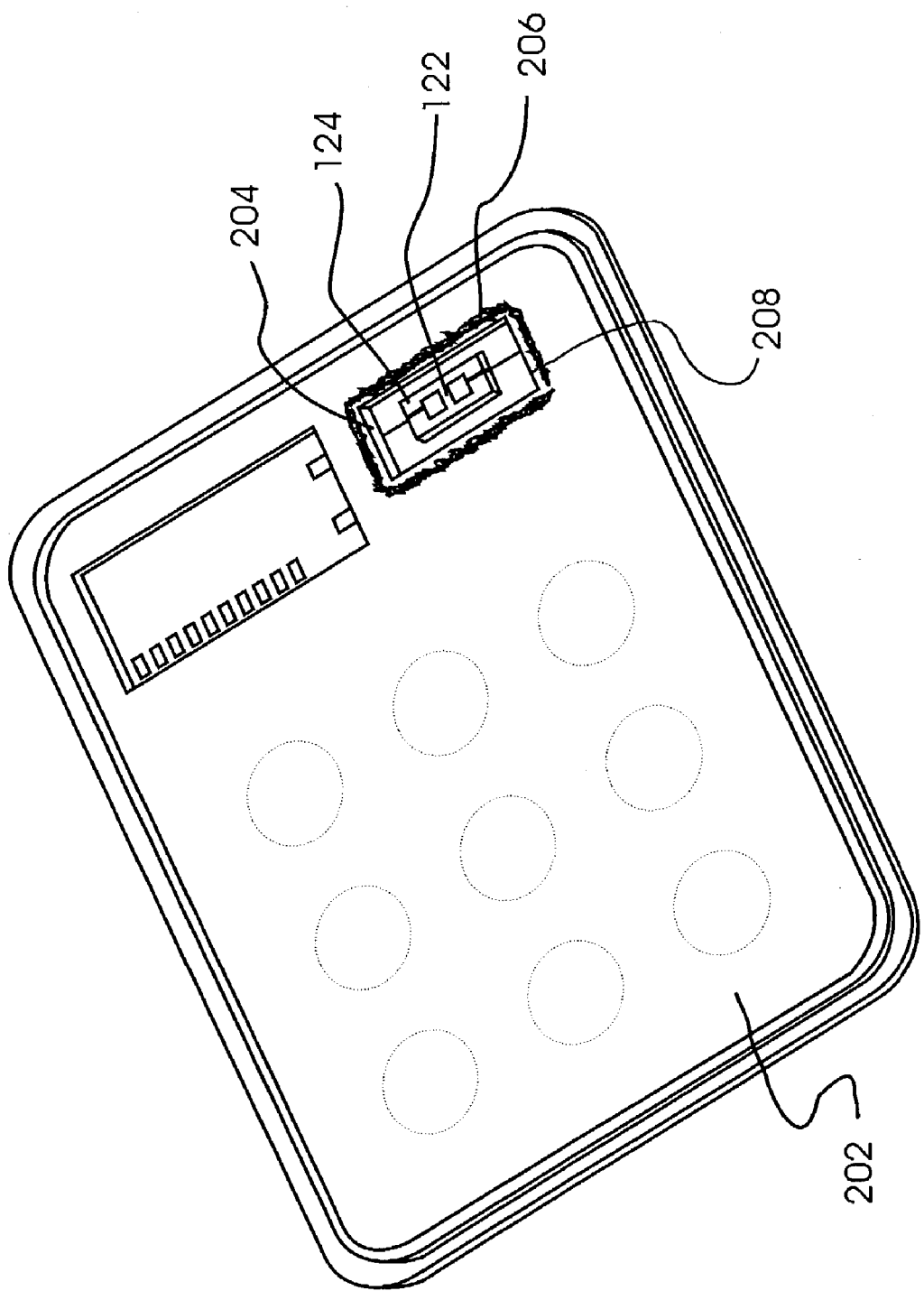
FIG. 2 illustrates the notional circuit scheme of the instrumented medication package shown in FIG. 1 to which a protective layer has been applied, allowing exposed contacts suitable for use in accordance with the present invention.

As shown in FIG. 2, a protective layer 202 may be placed over conductive traces 112 (not visible in present view), such that the traces 112 cannot be adversely affected during shipment or handling. A window 204 through the protective layer 202, exposing the discontinuity 122, may be provided to allow the discontinuity 122 to be bridged, such as by the addition of a conductive element (not shown) across the discontinuity 122. A mechanical switch such as a toggle switch may be joined to the pads to allow completion of the circuit, however the use of such a switch may reduce the efficiency of the packaging. Alternately, an adhesive, such as a pressure sensitive adhesive 206, may be placed around the perimeter 208 of the window 204, to allow an additional membrane or layer to be releasably attached to the instrumented medication package 102.

Where the instrumented medication package 102 is formed with a layer of adhesive 206 for attaching a conductive layer across the discontinuity 122, it may be beneficial to protect the adhesive 206 from being exposed to dirt prior to placement of a conductive element (not shown) across the discontinuity 122. A protective cover (not shown) may be provided, such that the protective cover covers the adhesive 206, the exposed ends 126, 128, and the discontinuity 122, while remaining only weakly bonded to the adhesive 206, such that the protective cover can be removed from the adhesive 206 without damaging or disturbing the adhesive 206 to the extent that adhesion of a conductive element to the instrumented medication package 102 would be prevented. Furthermore, as humid air may provide a sufficiently conductive path to allow a slow depletion of the power supply if the discontinuity 122 were exposed to the air for an extended period, the use of the protective layer as a barrier between the discontinuity 122 and the environment may extend the shelf life of the power supply.

Where the reverse surface of the protective cover is formed from a conductive material, reversal of the protective cover may provide the conductive element, such that the protective cover may be removed from the instrumented medication package, reversed, and re-adhered to the instrumented medication package 102 as a means of connecting the power supply 116 to the circuitry 104. Additionally, the side of the label in contact with the instrumented medication package when the switch label is in the on position may be treated to make the bond between the label and the instrumented medication package permanent.

Figure 3:
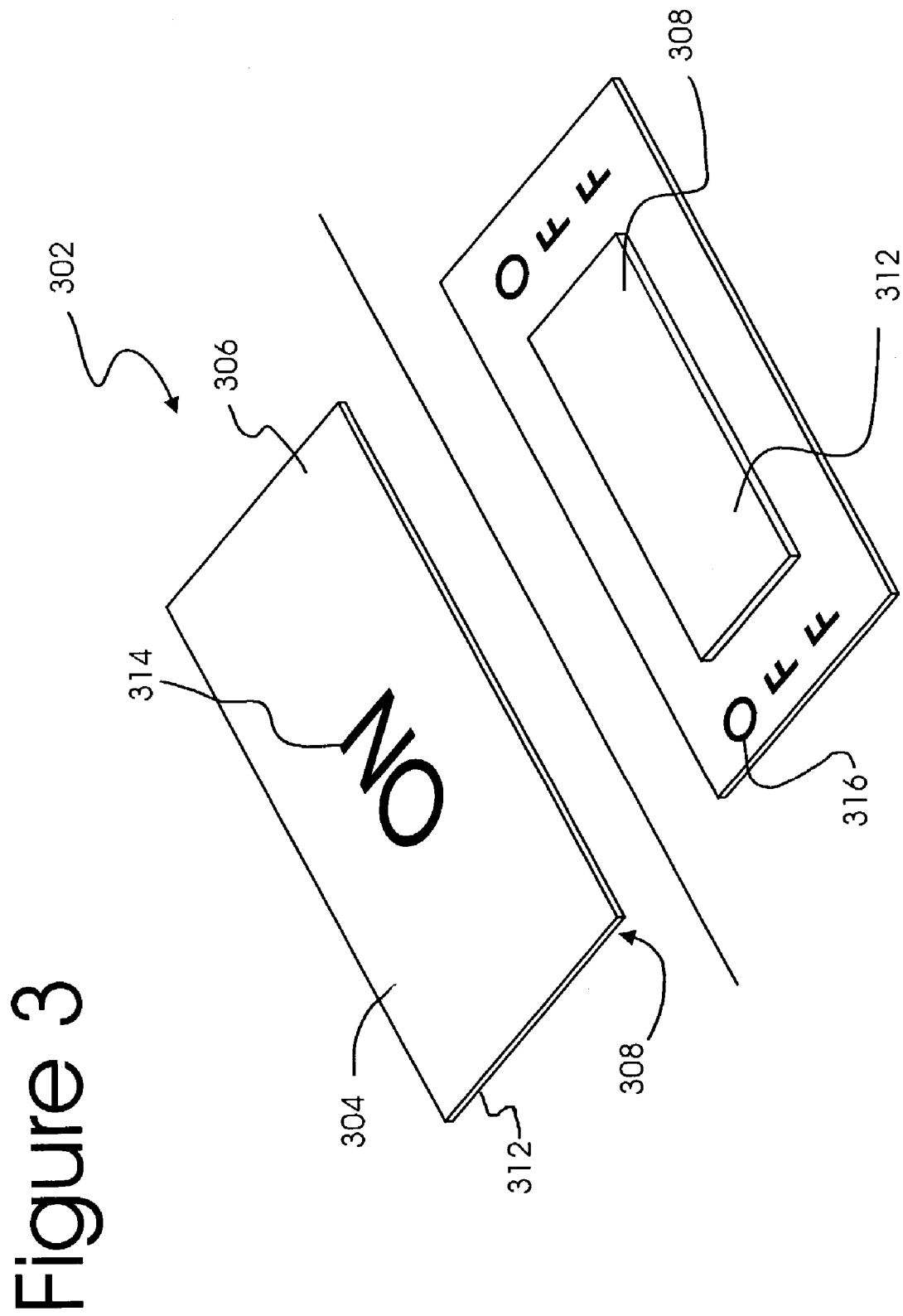
FIG. 3 illustrates a removable label suitable for alternately protecting and bridging the contacts shown in FIGS. 1 and 2.

As shown in FIG. 3, an element for electrically bridging the discontinuity 302 may be formed by a membrane 304 having an insulative layer 306, formed of an electrically non-conductive material, and a conductive layer 308, formed from an electrically conductive material, where each layer forms an outer surface 310, 312 to the completing membrane or "switch label" 304. The insulative layer 306 of the switch label 304 may extend beyond the borders 312 of the conductive layer 308, while the conductive layer 308 may form the conductive element. The two outer surfaces 310, 312 of the switch label 304 may be provided with indicia 314 (not shown) to indicate when the switch label 304 is positioned to complete the discontinuity 122.

Figure 4:
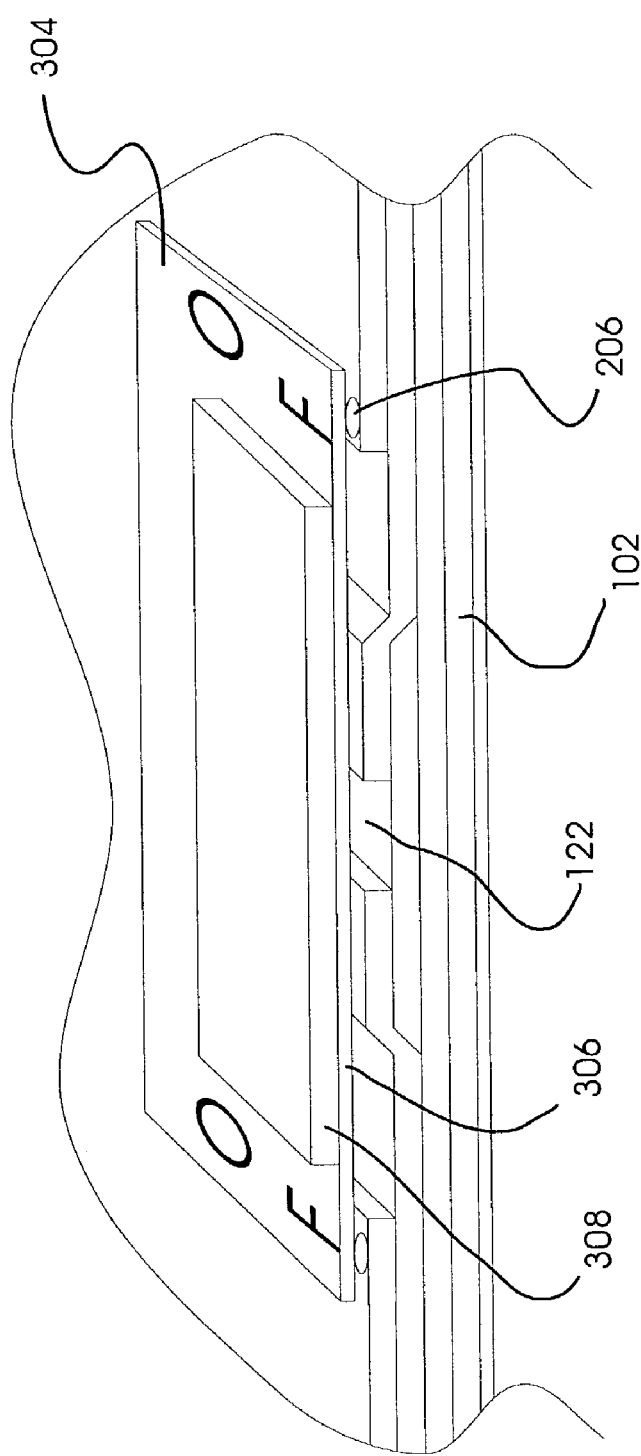
FIG. 4 shows a cross-sectional view of an instrumented medication package and a switch label such as shown in FIG. 3, wherein the switch label is in a circuit deactivated orientation.

FIG. 4 shows a switch label 304 which has been adhered to the instrumented medication package 102 with its insulative layer 306 facing the power supply trace discontinuity 122. When the insulative layer 306 of the switch label 304 is placed in contact with the power supply trace ends 126, 128, the discontinuity 122 in the power supply trace 118 is not completed, preventing the power supply 116 from being discharged. If the "off" indicia 316, as shown in FIG. 3, are placed on the side of the switch label 304 on the same side as the side exposing the conductive layer 308, the switch label 304 when attached to the instrumented medication package 102 will display the "off" indicia 316 when the instrumented medication package 102 is viewed.

Figure 5:
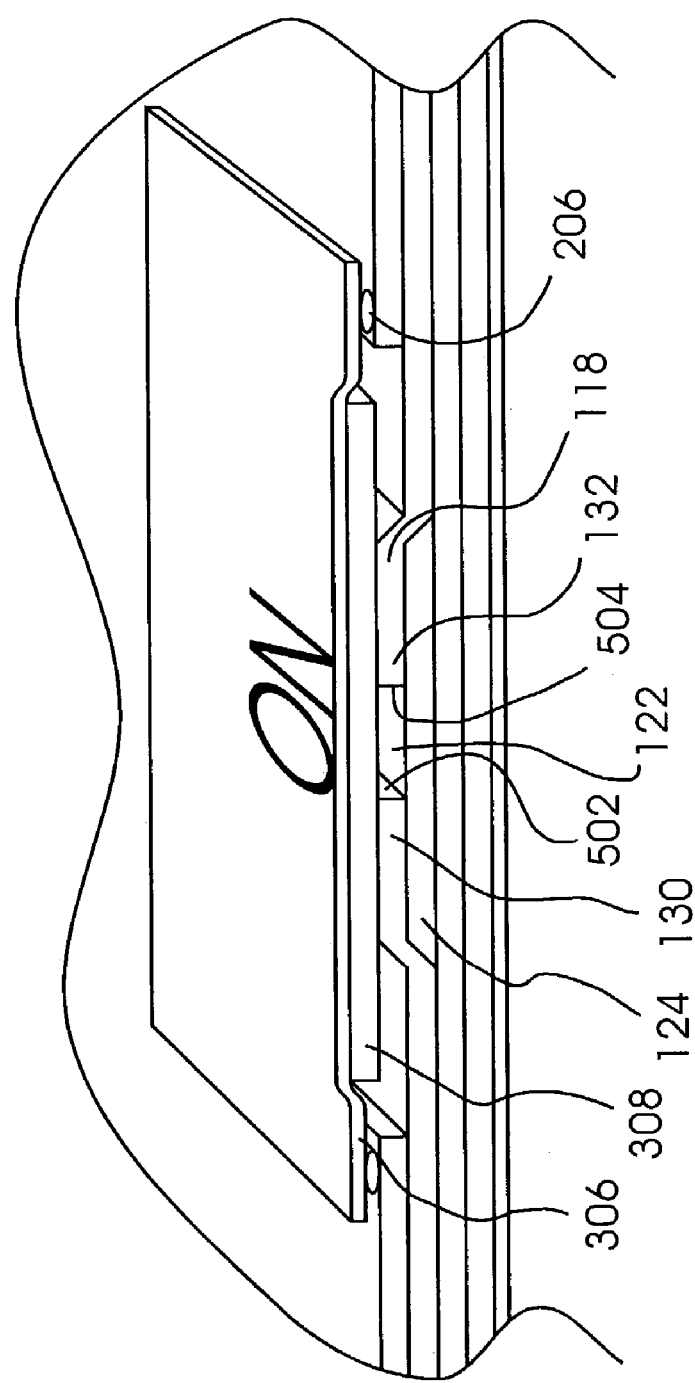
FIG. 5 shows a cross-sectional view of an instrumented medication package and a conductive label such as shown in FIG. 3, wherein the switch label is in a circuit activated orientation.

In FIG. 5, a switch label 304 is shown adhered to the instrumented medication package 102 with its conductive layer 308 facing the power supply trace 118 discontinuity 122. When the conductive layer 308 of the switch label 304 is placed in contact with the power supply trace ends 126, 128, the discontinuity 122 in the power supply trace 118 is completed by contact between the conductive layer 308 and the power supply trace ends 126, 128 at the edges of the discontinuity 122. The use of pads 130, 132, expanding the surface area of the ends 126, 128 of the power supply trace 118 at the edges 502, 504 of the discontinuity 122 increase the surface contact between the conductive layer 308 and the ends 126, 128 of the power supply trace 118. By raising the ends 126, 128 of the trace at the edges 502, 504 of the discontinuity 122, such as by placing a block 124 of insulative material as shown in FIGS. 1 and 2, contact between the conductive layer 308 and the ends 126, 128 of the power supply trace 118 adjacent to the discontinuity 122 may be improved, improving the reliability of the switch label 304 as a means for alternately connecting or disconnecting the power supply 116 to the instrumented medication package 102 circuitry 104. Additionally, indicia 314 signifying the "on" position of the switch label may be displayed when the instrumented medication package 102 is viewed.

Figure 6:
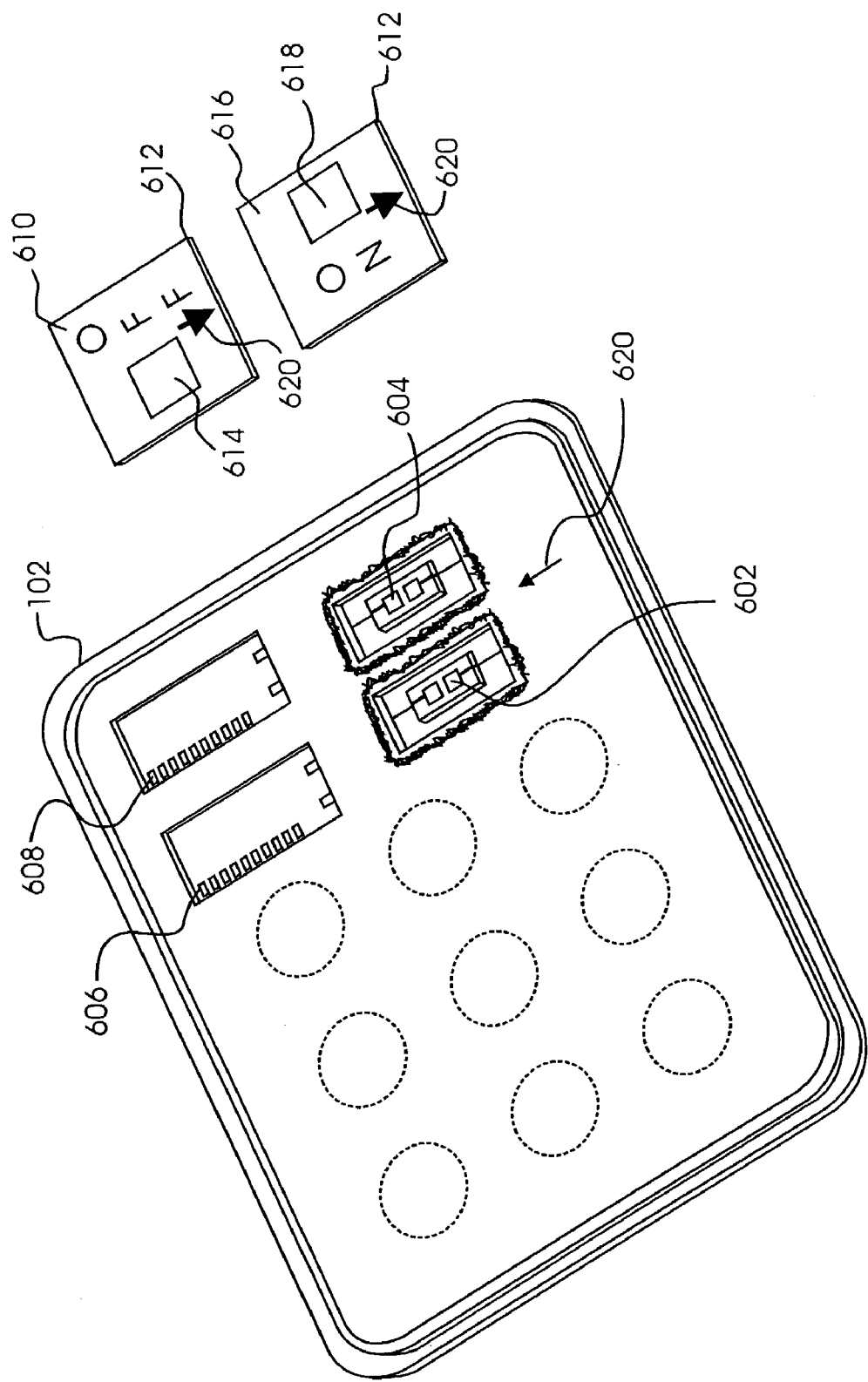
FIG. 6 shows a reusable switch label suitable for alternately bridging first and second sets of contacts.

As shown in FIG. 6, a switch label may be formed to allow alternate actuation of a first 602 or a second 604 set of contacts. Such a configuration may be useful when different circuits (i.e., 606, 608) are used at different times, such as when passive radio frequency identification circuitry is used before an instrumented indication package 102 is dispensed, while active circuitry is used and after the package 102 is dispensed. A first side 610 of switch label 612 could have a conductive outer layer 614 positioned to contact the first set of contacts 602, while the reverse side 616 of the switch label 612 could have a conductive layer 618 positioned to contact the second set of contacts 604. Indices 620 could be provided to indicate correct orientation of the switch label 612 on the package 102 to ensure that the correct set of contacts are bridged based on the side of the switch label applied.

The present invention may be embodied in other specific forms than the embodiments described above without departing from the spirit or essential attributes of the invention. Accordingly, reference should be made to the appended claims, rather than the foregoing specification, as indicating the scope of the invention.

What is claimed is:

1. An instrumented medication package, said instrumented medication package comprising a power supply, circuitry for monitoring at least one condition associated with the instrumented medication package, and a connective path between said power supply and said circuitry;
   wherein said connective path comprises a switch, said switch for alternately conductively connecting or disconnecting said power supply from said circuitry;
   wherein said connective path comprises a discontinuity and at least two contacts adjacent to said discontinuity, and said switch comprises a means for selectively bridging the discontinuity between the contacts;
   wherein said switch comprises a conductive membrane placeable across the discontinuity to provide a conductive path between said contacts; and
   wherein said conductive membrane comprises first and second surfaces, said first surface being electrically conductive, said second surface being electrically non-conductive, wherein said first and said second surfaces form first and second exterior surfaces of the conductive membrane, and wherein said power supply may be alternately connected or disconnected by placing the electrically conductive or electrically non-conductive surface in contact with the contacts.

2. In an instrumented medication package having at least one power supply trace for conductively connecting a power supply to circuitry associated with said instrumented medication package, an electrical current flow control, said electrical current flow control comprising:
   a discontinuity in said power supply trace;
   a protective layer over said power supply trace, said protective layer having a window exposing said discontinuity; and
   a completion element, said completion element comprising a conductive material;
   wherein said power supply trace has a first and a second end adjacent to said discontinuity; and wherein said completion element is attachable to said instrumented medication package across said discontinuity, said completion element providing an electrically conductive path when attached to said instrumented medication package across said discontinuity.

3. An instrumented medication package according to claim 2, wherein said completion element further comprises adhesive placed adjacent to a periphery of said completion element, said adhesive for attaching said completion element to said instrumented medication package across said discontinuity.

4. An instrumented medication package according to claim 3, wherein said instrumented medication package further comprises an adhesive adjacent to said discontinuity, said adhesive for attaching said connection element to said instrumented medication package across said discontinuity.

5. An instrumented medication package according to claim 4, said completion element comprising a switch label, said switch label comprising an insulative layer and a conductive layer, and wherein said adhesive for attaching said completion element comprises a releasable adhesive.

6. An instrumented medication package according to claim 5, wherein said switch label further comprises indicia on at least one surface, said indicia indicating a state of the discontinuity when said switch label is attached to said instrumented medication package across said discontinuity.

7. An instrumented medication package according to claim 4, further comprising a spacer block interposed between said instrumented medication package and said first and second ends, said spacer block formed of a non-conductive material.

8. An instrumented medication package according to claim 7, wherein said window exposes said discontinuity and extends beyond a periphery of said spacer block, such that said discontinuity is displaced above the surface of the instrumented medication package through the window.

9. An instrumented medication package according to claim 2, wherein said first and said second ends of said power supply trace comprise pads, said pads increasing the exposed surface area of said first and said second ends adjacent to the discontinuity.

* * * * *